(12) United States Patent
Biber

(10) Patent No.: US 9,910,116 B2
(45) Date of Patent: Mar. 6, 2018

(54) METHOD AND TEST APPARATUS FOR DETERMINING A DEVIATION IN HOMOGENEITY OF A MAGNETIC FIELD OF A MAGNETIC RESONANCE SCANNER

(71) Applicant: Siemens Healthcare GmbH, Erlangen (DE)

(72) Inventor: Stephan Biber, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/466,010

(22) Filed: Mar. 22, 2017

(65) Prior Publication Data

US 2017/0276746 A1    Sep. 28, 2017

(30) Foreign Application Priority Data

Mar. 23, 2016  (DE) .................. 10 2016 204 863

(51) Int. Cl.
*G01R 33/387*    (2006.01)

(52) U.S. Cl.
CPC ................................ *G01R 33/387* (2013.01)

(58) Field of Classification Search
CPC ......................................... G01R 33/42–33/421
USPC ................................................... 324/300–322
See application file for complete search history.

(56) References Cited

U.S. PATENT DOCUMENTS

| | | | |
|---|---|---|---|
| 5,055,791 A | 10/1991 | LeRoux et al. | |
| 7,944,209 B2* | 5/2011 | Abe ................. | G01R 33/56563 324/309 |
| 9,274,191 B2* | 3/2016 | Biber ................. | G01R 33/3875 |
| 9,588,200 B2* | 3/2017 | Sakakibara ........ | G01R 33/3873 |

FOREIGN PATENT DOCUMENTS

WO    WO-2014/097056 A1    6/2014

* cited by examiner

*Primary Examiner* — Melissa Koval
*Assistant Examiner* — Rahul Maini
(74) *Attorney, Agent, or Firm* — Schiff Hardin LLP

(57) ABSTRACT

In a method and test apparatus for determining a deviation in the homogeneity of a basic magnetic field of a magnetic resonance scanner, test vessels are positioned in a test plane that first and second positions along a direction in the scanner, and measurement data are acquired with the test vessels at said respective positions. The acquired measurement data are provided to a processor, wherein a deviation of the homogeneity of the basic magnetic field is determined based thereon.

13 Claims, 4 Drawing Sheets

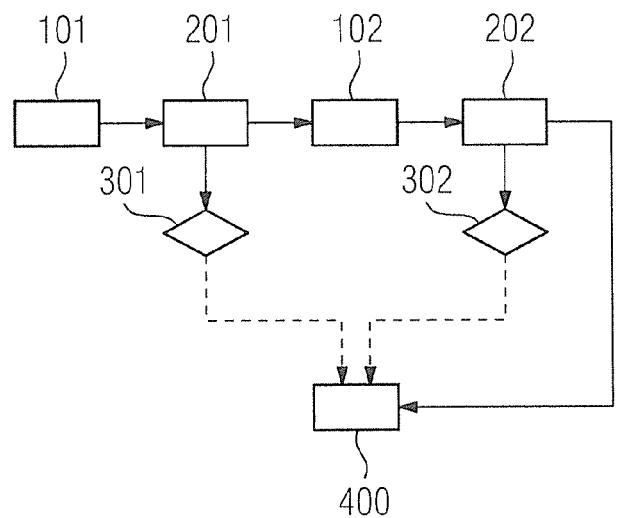
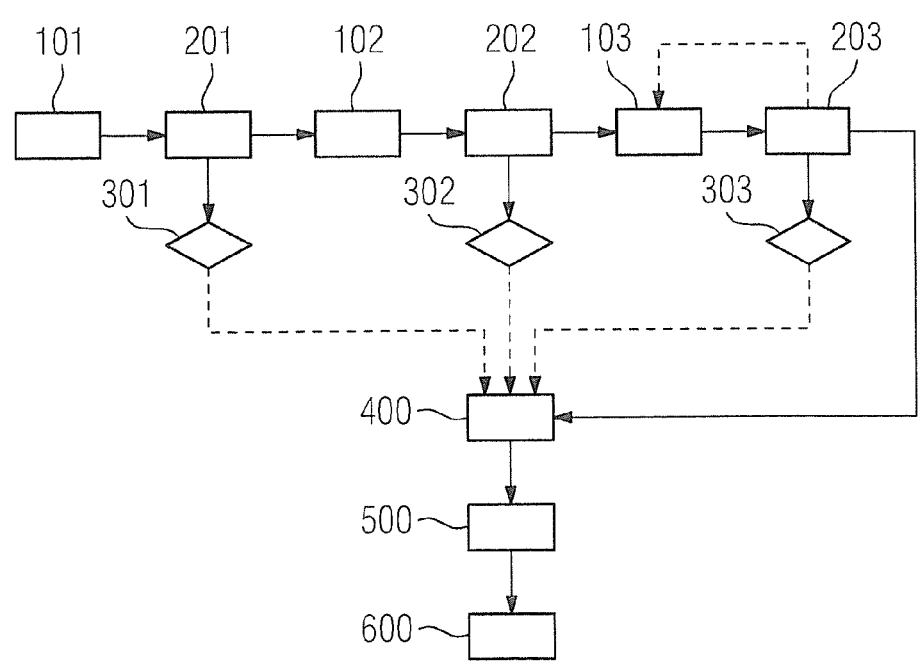

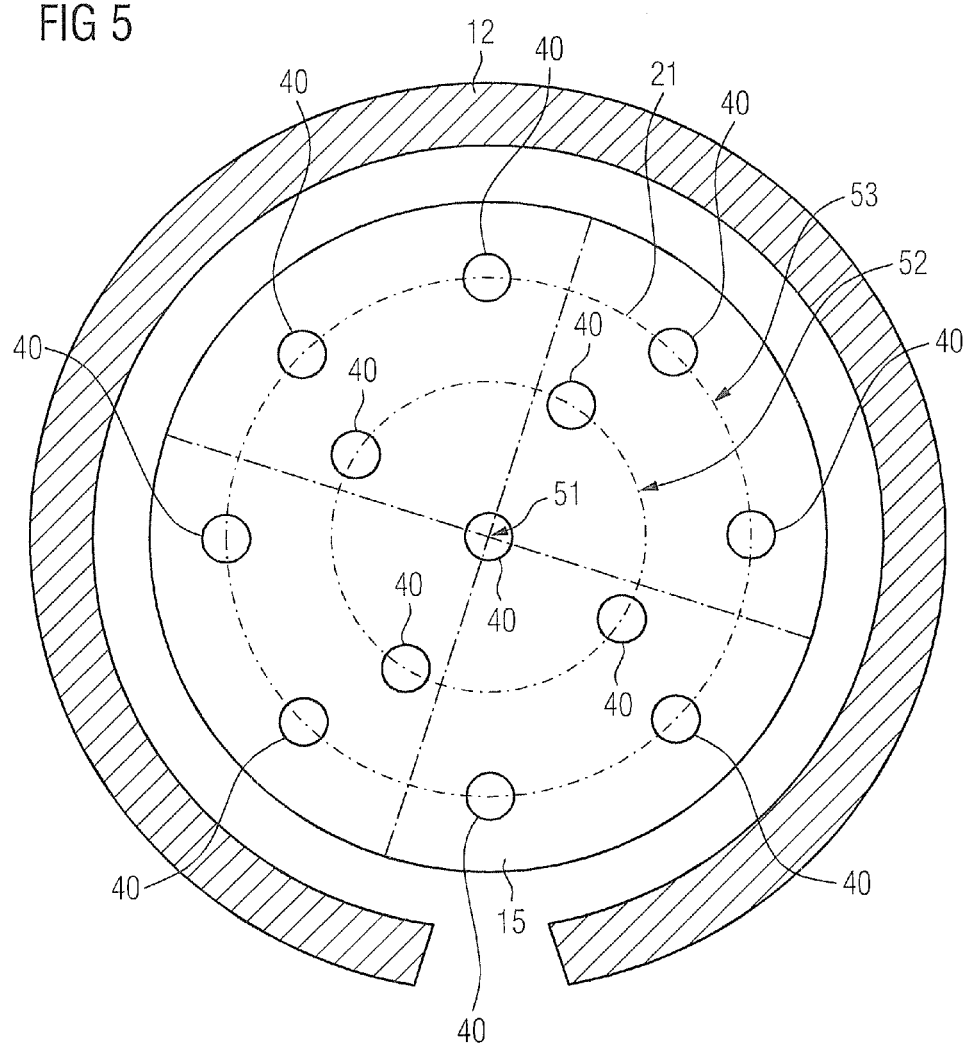

METHOD AND TEST APPARATUS FOR DETERMINING A DEVIATION IN HOMOGENEITY OF A MAGNETIC FIELD OF A MAGNETIC RESONANCE SCANNER

BACKGROUND OF THE INVENTION

Field of the Invention

The invention concerns a method for determining a deviation in homogeneity of a magnetic field of a magnetic resonance scanner in a direction defined by an axis, as well as a test apparatus for implementing such a method.

Description of the Prior Art

In magnetic resonance scanners, the examination subject that is to be scanned, a patient for example, is typically exposed to a relatively high basic magnetic field, of 1.5 or 3 tesla for example, with the use of a basic field magnet. In addition, at least one magnetic field gradient is applied by a gradient coil unit. Radio-frequency excitation signals (RF signals) are then transmitted via a radio-frequency antenna unit by suitable antenna equipment for the purpose of tipping the nuclear spins of specific atoms excited into resonance by the radio-frequency field through a defined flip angle with respect to the magnetic field lines of the basic magnetic field. During the resulting precession of the nuclear spins, radio-frequency signals, also known as magnetic resonance signals (MR signals), are emitted, received by suitable reception coils, and then processed further to produce image data. The quality of the image data is influenced by the homogeneity of the basic magnetic field and the at least one magnetic field gradient. If the basic magnetic field and/or the magnetic field gradient exhibit local deviations, the image data may have no MR signal or a distorted MR signal at certain positions. The homogeneity of the basic magnetic field in the examination region of interest is particularly important. The examination region of interest is the term used to denote the area of the magnetic resonance scanner in which MR signals may be acquired from the examination subject without repositioning the examination subject.

During the installation of a magnetic resonance scanner, a calibration of the basic magnetic field generated by the basic field magnet is typically carried out and, based on the results, metal, for example, is placed in the scanner such that deviations in the homogeneity of the basic magnetic field are reduced. Similarly, the homogeneity of the at least one magnetic field gradient may be checked and/or improved during installation of the magnetic resonance scanner. This process is referred to as "shimming". A magnetic field or the local deviations thereof is or are measured by a shim device. For that purpose, data are typically acquired at a number of (preferably strictly defined) positions of the magnetic field.

SUMMARY OF THE INVENTION

An object of the invention is to provide a robust and reliable method for determining a deviation in homogeneity of a magnetic field of a magnetic resonance scanner. A further object of the invention is to provide a test apparatus for use in implementing a method of that type.

The inventive method determines a deviation in homogeneity of a magnetic field of a magnetic resonance scanner in a direction defined by an axis, using at least two test vessels that are arranged on a test plane perpendicular to the direction.

The method includes positioning the test plane at a first position of the axis, wherein a first test vessel is arranged at a first location of the first test vessel and a second test vessel is arranged at a first location of the second test vessel. First measurement data induced by the test vessels at their first locations are recorded. The test plane is then repositioned at a second position of the axis that is different from the first position in one coordinate of the axis, so the first test vessel is arranged at a second location of the first test vessel and the second test vessel is arranged at a second location of the second test vessel. Second measurement data induced by the test vessels at their second locations are recorded. The deviation in the homogeneity of the magnetic field is determined in a processor, which is provided with the first and second measurement data, based on at least the first and the second measurement data. The determined deviation is made available from the processor as an electronic output.

Magnetic fields typically generated by a magnetic resonance scanner are the static basic magnetic field and gradient fields. The magnetic field taken into consideration in the method according to the invention may relate to the static basic magnetic field and/or to a gradient field. Typically, the static basic magnetic field is a vector field that has a defined amplitude, for example 1.5 T or 3 T, in a first direction. The vector field is preferably aligned exclusively in the aforementioned direction. This direction is defined by the axis such that the direction points parallel to the first axis. A gradient field is typically also a vector field that is aligned parallel to this axis. In contrast to the static basic magnetic field, the amplitude of the gradient field is dependent on spatial position within the scanner. Typically, the amplitude of the gradient field is modulated linearly in one direction, for example in the aforementioned axis-defined direction, or in a direction perpendicular to that direction. The gradient of the gradient field in this direction, which may be referred to as a magnetic field gradient, is homogeneous within the examination region of interest. A gradient field is referred to as homogeneous when its magnetic field gradient is homogeneous.

In the method according to the invention, at least two test vessels are used. The test vessels are preferably hermetically sealed and/or filled with a substance, in particular a liquid. The test vessels may be filled with different substances. The liquid preferably includes the atomic nuclei that are to be excited by the magnetic resonance scanner, typically the atomic nuclei of hydrogen atoms. The test vessels may also be designed such that they determine the strength of the magnetic field at their location without a magnetic resonance scan being conducted. This is possible, for example, if each of the test vessels is a Hall probe.

The at least two test vessels are arranged such that they lie in a test plane that is orthogonal to the aforementioned axis, in particular perpendicular to the axis-defined direction. All the test vessels used in the method preferably lie in the test plane. The test vessels are preferably distributed in the test plane such that, given appropriate positioning of the test plane in a plane in the examination region, they are situated in the examination region. The test vessels are preferably so numerous and/or distributed in the test plane such that, given appropriate positioning of the test plane in a plane in the examination region, they cover the examination region in the plane to a degree so that the measurement data produced by the test vessels in the plane suffices for determining the deviation in the homogeneity of the magnetic field in the plane. Accordingly, there is no need, for example, to record further measurement data following a rotation of the test plane around the axis-defined direction. The examination region typically has a spatial extent in the axis-defined direction that is greater than the spatial extension of the test vessels in that direction.

In a first method step, the test plane is positioned at a first position by the test vessels being arranged at the first position of the axis-defined direction. The first position is preferably encompassed by the examination region in that direction. The first locations of the first and the second test vessels preferably lie in the examination region. In a second method step, measurement data are acquired. The measurement data are generated by the at least two test vessels while the test vessels are positioned at the first locations. In order to record the measurement data, a substance contained in both test vessel or in the test vessels is typically excited initially by excitation signals emitted by the scanner in order to thereafter record MR signals. Measurement data may be MR signals and/or a measure of the amplitude, in other words the strength of the magnetic field. The MR signals are typically received by at least one reception coil. Preferably, the individual test vessels are each enclosed by at least one reception coil.

The first and second method steps are repeated, but with the test plane at a second position. Compared to the first position, the second position is shifted along the axis in the axis-defined direction. Displacement in the positive or negative direction is possible. The positioning of the test plane at the first and/or the second position may be carried out manually. An operator or technician who executes the method according to the invention may manually place the test vessels, which may be held in a retaining fixture, at the first and/or the second position and thus specify the position of the test plane. The retaining fixture may in this case be mounted on a patient table, for example.

After the first and second sets of measurement data have been recorded, these are processed by a determination processor. A measure for the deviation in the homogeneity may be determined at the same time based on the measurement data. Preferably, the amplitude of the MR signals at the first and the second locations of the at least two test vessels is determined for this purpose. Based on the MR signals, the homogeneity of the magnetic field and/or deviations therefrom are determined preferably in the entire examination region, or at least in the patient receiving zone. The determined homogeneity and/or deviations therefrom are preferably made available with a spatial resolution (distribution).

An advantage of the method according to the invention is that when the test vessels are repositioned, they maintain their position within the test plane. In particular, the method dispenses with a rotation of the test plane when the test plane is positioned at the second position compared to the first position. For the positioning at the second position, a displacement along the axis is required, which may be carried out manually, for example, with sufficient accuracy with the assistance of a distance meter.

Typically, at least one cable-based connection is required between a reception coil and further units of the magnetic resonance scanner. Preferably, at least one reception coil is arranged in a fixed spatial relationship to the test vessels. A high MR signal can be achieved if each test vessel is enclosed by a reception coil. If the test vessels are arranged fixedly in the test plane and the positioning of the test vessels in the second position is effected by a linear displacement in the first direction, the cable connection typically can be completed subsequently without difficulty. Dispensing with a rotation about the axis during the repositioning allows a simple embodiment of the test vessel arrangement. One retaining fixture for the test vessels may be sufficient for arranging the test vessels and positioning the test plane. This enables the test vessels to be implemented with a simple mechanical design. As a result, the arrangement of the test vessels may be realized in a low-cost embodiment. The test vessels, inclusive of the retaining fixture where applicable, are thus resistant to disruptions during transportation and installation, and thus can be used without extensive expertise in handling the test vessels.

In an advantageous embodiment of the method, the test plane is positioned at at least one further position of the first axis, this further position being different from the first and the second position in one coordinate of the axis, and the first test vessel is arranged at at least one further location of the first test vessel and the second test vessel is arranged at at least one further location of the second test vessel. Further measurement data produced by the test vessels at their further locations are recorded. The deviation in the homogeneity of the magnetic field is determined in the processor based on at least the first, the second and the further measurement data.

According to this embodiment, the test vessels are placed at multiple positions and consequently at a number of locations at which measurement data are acquired. The volume of measurement data used in order to determine the deviation in the homogeneity typically increases with the number of test vessels and the number of locations thereof. With an increasing volume of measurement data, it is possible to increase the precision of the determined deviation in the homogeneity.

In another embodiment of the method, a number of shim elements and/or their spatial distribution are/is determined based on the deviation in the homogeneity of the magnetic field in order to increase the homogeneity of the magnetic field. The determined deviation in the homogeneity may accordingly be used to determine and implement measures that increase the homogeneity of the magnetic field. The spatial distribution of the magnetic field and/or the spatial distribution of deviations from the homogeneity of the magnetic field may be reduced or eliminated by placing shim elements, for example plates made of a certain material, in the housing of the magnetic resonance scanner in the vicinity of the basic field magnet and/or the gradient coil unit. A metal such as iron is typically used as the material. Based on the measurement data, the number, position and/or material that, positioned on/in the magnetic resonance scanner, can increase the homogeneity of the magnetic field, may be determined by the determination processor, for example. The thus determined number, position and/or material may be arranged on the magnetic resonance scanner by an installation engineer, for example. An advantage of this embodiment is that the result of the measurement is used in order to actively increase the homogeneity of the magnetic field and thereby improve the quality of the image data that are to be recorded.

In a further embodiment of the method, the test vessels are mounted on a retaining fixture that is arranged on a patient table and can be positioned by the patient table at at least the first and the second position. The material of the retaining fixture is preferably designed/selected such that it does not interact with the basic magnetic field and/or the gradient field. Wood and/or plastic, for example, may be used as the material for the retaining fixture. The retaining fixture arranges the test vessels preferably fixedly, in the test plane such that a positioning of the retaining fixture in the first position or in the second position places the test vessels at the corresponding first and/or second locations. The retaining fixture may be arranged, such as by being supported or mounted, on the patient table. Typically, the patient table is designed to execute a displacement in the aforementioned direction so that an examination subject can be moved from outside of the magnetic resonance scanner into the examination region. As the examination subject, the test vessels and the retaining fixture can be moved into the examination region and assume the first and/or second position. The patient table is typically displaced automatically, for example on the basis of a digital specification by an operator of the magnetic resonance scanner. Accordingly, the retaining fixture and the test vessels can be moved exactly in the direction so that it can be ensured that the second position differs from the first position by one coordinate on the axis, while the other coordinates are preferably unchanged. This method accordingly requires a manual positioning of the retaining fixture holding the test vessels in the test plane on the patient table. The positioning of the test plane at at least the first and the second position may be effected by means of a precise specification, for example by digital input at a user interface of a computer or by a predefined computer program. As a result, the positioning can be performed very precisely, and deviations in the homogeneity can be determined with greater accuracy. The method can be automated, thereby reducing manual influences and consequently the susceptibility to error.

In another embodiment of the method, the patient table executes a continuous movement and the test plane assumes the first position at a first point in time and the second position at a second point in time with no interruption to the continuous movement. The patient table is typically supported and drivable such that it is able to perform a continuous movement in a defined region along the first axis. The examination subject thus may be conducted through the examination space while the magnetic resonance scanner transmits RF signals and gradient fields and acquires MR signals. The spatial extent of the examination region is important here, because MR signals from this region may be spatially encoded and received. The continuous movement of the patient table in the first direction may be combined with the method according to the invention such that the test plane assumes at least the first position, the second position and, where necessary, further positions in each case at a point in time at which MR signals of the test vessels are generated and recorded.

The positions, in particular the first and the second position, at which measurement data are recorded are preferably determined prior to commencement of the method according to the invention. The positions may be specified automatically, for example, on the basis of the design of the test apparatus and/or on the basis of the volume within which a deviation in the homogeneity of the magnetic field is to be determined. The positions may also be specified by a specification by a user. It is possible for the continuous table movement to enable an automated or standardized method having a short duration.

In another embodiment of the method, the test vessels are designed in a spherical shape. Susceptibility differences, at transitions between two different materials for example, may detrimentally affect the homogeneity of a magnetic field, in particular of the basic magnetic field, when the two different materials are situated in the magnetic field. The surface of the test vessels is typically plastic and the test vessels are typically filled with a liquid and surrounded by air. If, accordingly, the test vessels are situated in a magnetic field, these three adjoining materials typically exhibit different susceptibilities and generate changes in the magnetic field. Sphere-shaped surfaces, which exhibit a different susceptibility compared to their environment, have less influence on the homogeneity of a magnetic field than many surfaces having other shapes. The diameter of the sphere-shaped test vessels is preferably at least 0.5 cm and/or at most 5 cm. The test vessels are preferably arranged symmetrically with respect to the test plane. An advantage of the method having test vessels embodied in such a way is a reduced influence of test vessels on the magnetic field of which the homogeneity is to be quantified in accordance with the inventive method. This enables the precision of the measurement data to be increased and consequently the deviation in the homogeneity of the magnetic field to be determined more accurately.

In another embodiment of the method, the measurement data induced by the at least two test vessels are recorded by a reception coil unit. Accordingly, the MR signal induced in the test vessels is preferably not acquired by a reception coil surrounding a respective test vessel, but by a reception coil unit that has a reception sensitivity in the range of the at least two test vessels. In this embodiment of the method, the reception coil unit may be a commercially available local reception coil, for example a flexible coil that is used in hip examinations of patients. If such a reception coil unit is employed, the method according to the invention requires no further units specifically produced for the method, in particular no electronic components, in addition to the test vessels and where applicable the retaining fixture. The method may accordingly be implemented at reasonable cost. A good level of quality in the determination of the deviation in the homogeneity can nonetheless be achieved on account of a reception coil unit having high sensitivity. Commercial reception coils are typically connectable to the magnetic resonance scanner in a user-friendly manner. Accordingly, in this embodiment, connecting the reception coil unit and configuring the test vessels prior to commencement of the method according to the invention may be managed in a less complex manner and as a result is rendered less prone to error.

In another embodiment of the method, the reception coil unit is arranged on a retaining fixture for the test vessels. When the test vessels are arranged on such a retaining fixture, the reception coil unit may be arranged directly on the retaining fixture, for example. As a result, a high intensity of the MR signals can be ensured.

In another embodiment of the method, at least five test vessels are arranged in a circle on the test plane. The test vessels may be arranged on a perimeter of the circle. The center point of the circle is preferably arranged in the center of the intersection area of the examination region having a plane perpendicular to the first axis. In a circular arrangement of the test vessels and positioning at at least two different positions along the first axis, measurement data may be acquired along the lateral surface area of a cylinder. Based on measurement data of this type, the homogeneity of the magnetic field in the examination region may be determined particularly efficiently with the use of the Bessel functions, for example.

In another embodiment of the method, the test vessels are arranged on at least two concentric circles. The center point of the at least two concentric circles is preferably arranged in the center of the intersection area of the examination region having a plane perpendicular to the first axis, preferably the test plane. According to this embodiment, the test vessels may consequently be arranged particularly well distributed on the test plane. For example, at least three test vessels can be arranged on the outer of the at least two concentric circles and at least two test vessels can be arranged on the inner of the at least two concentric circles. With such an arrangement of the test vessels and the positioning at at least two different positions along the first axis, given appropriate choice of the first and second locations, measurement data may be acquired on a spherical surface. Based on measurement data of this type, the homogeneity of the magnetic field in the examination region may be particularly accurately determined with the use of the spherical functions, for example. A point-symmetrical arrangement of the test vessels is likewise advantageous. The test vessels may be arranged for example at the vertices of at least one regular polygon. An arrangement of the test vessels at the vertices of a number of regular polygons is advantageous for determining the homogeneity of the magnetic field in the examination region when the multiple regular polygons are concentric to one another.

In another embodiment of the method, the test vessels are arranged, and the at least two positionings of the test plane are effected, such that a variable subset of the locations of the test vessels of the at least two positions of the test plane is arranged on a spherical surface. The locations of the test vessels that, according to this embodiment, are arranged on the spherical surface, are preferably uniformly distributed on the spherical surface. In particular, the subset of the test vessels lying on the spherical surface is dependent on the position of the test plane. Measurement data of test vessels not lying on the spherical surface may be recorded and used to improve the determination of the deviation in the homogeneity. It is also possible to dispense with the recording of measurement data of this type.

It is advantageous to position the test plane at more than two positions of the position-defining axis. An arrangement of the test vessels described in this embodiment variant may be achieved for example by the arrangement of the test vessels on multiple, for example four, concentric circles. Upon positioning the test plane, seven positions may be chosen at intervals from one another such that one circle in each case of the four concentric circles is arranged on the surface of a virtual sphere. Based on such measurement data, the homogeneity of the magnetic field in the examination region may be determined particularly accurately with the use of the spherical functions, for example. The measurement data of the locations that do not lie on the spherical surface may be used to make the result of the method, i.e. the deviation in the homogeneity, more precise. The more test vessels that are arranged in the test plane, the more measurement data may be acquired, and the more accurately the deviation in the homogeneity may be determined.

The invention furthermore concerns a test apparatus for use in the method according to the invention for determining a deviation in homogeneity of a magnetic field of a magnetic resonance scanner in a direction, wherein the test apparatus has at least two test vessels that are arranged on a test plane perpendicular to that direction.

The test apparatus enables a robust method having little susceptibility to error to be performed for the purpose of determining a deviation in homogeneity of a magnetic field of a magnetic resonance scanner. In particular, a rigid arrangement of the test vessels in the test plane, for example by a retaining fixture, is sufficient and in the case of the test apparatus a unit permitting a rotation of the test vessels may be dispensed with. This enables cables connecting the test apparatus to the magnetic resonance scanner, for example, to be routed in a straight line. This enables the test apparatus to be embodied such that it has no components that move relative to one another. In particular, no movement of individual component parts incorporated in the test apparatus relative to one another is necessary when the method is performed. Rather, the test apparatus as a whole may be arranged at different positions. As a result, the test apparatus is particularly stable. Consequently, it is well suited for use in the installation of different magnetic resonance scanners and the transportation to the magnetic resonance scanners that are to be installed, without the possibility of the test apparatus being easily damaged. Equally, operating a test apparatus of this type is less complex and if necessary it may also be operated by users with little or no training in accordance with an accompanying operating guide.

The advantages of the test apparatus according to the invention substantially correspond to the advantages of the method according to the invention, as set forth in detail above. Features, advantages and alternative embodiments mentioned in this context are applicable to both aspects of the invention.

In an embodiment of the test apparatus, the test apparatus has at least two different materials, which materials are joined to one another such that they may be separated from one another at a predetermined separation point. A test apparatus for use in the method according to the invention for determining a deviation in homogeneity of a magnetic field of a magnetic resonance scanner is typically employed during installation of the magnetic resonance scanner at the installation site. Once the method has been completed, and the homogeneity of the magnetic field optimized, the magnetic resonance scanner typically transitions into a standard mode of operation. At that point it is typically no longer necessary to perform the method according to the invention for the magnetic resonance scanner at that site. As a consequence, the test apparatus according to the invention is preferably no longer required at that site.

If the test apparatus has predetermined separation points at which different materials are joined to one another, the materials are preferably easily separable from one another. A predetermined separation point may be, for example, a screwed connection, an adhesive bond or a clamped joint. Materials that are joined together by predetermined separation points of this type may be separated from one another as necessary, without damage, for example by mechanically releasing the screws or the clamped joint. Such a test apparatus may be dismantled or separated at at least one predetermined separation point in order to be transported from deployment at a first site to a further site. The transportation is simplified as a result.

The test apparatus preferably uses materials that may be disposed in normal household waste disposal. The materials are of the type classified as non-hazardous. Furthermore, such materials will not interact with a magnetic field generated by the magnetic resonance scanner. The test vessels may be molded from plastic, for example, and filled with a sodium chloride solution. If the test apparatus includes a retaining fixture, the material thereof may be composed, for example, of cellulose and/or plastic. If the cited different materials are separable from one another by predetermined separation points, then the materials may be separated from one another following the performance of the method according to the invention and preferably following termination of the shim process. The materials then can be disposed of and/or recycled. The test apparatus may accordingly be used one time only for a shim process and disposed of directly at the site of that process. There is no need for the test apparatus to be transported between different sites and/or to undergo maintenance. Logistics costs can be reduced as a result.

BRIEF DESCRIPTION OF THE DRAWINGS

FIG. 2 is a flowchart of a first embodiment of the method according to the invention.

FIG. 3 is a flowchart of a second embodiment of the method according to the invention.

FIG. 5 a schematically illustrates a test apparatus according to the invention.

DESCRIPTION OF THE PREFERRED EMBODIMENTS

Figure 1:
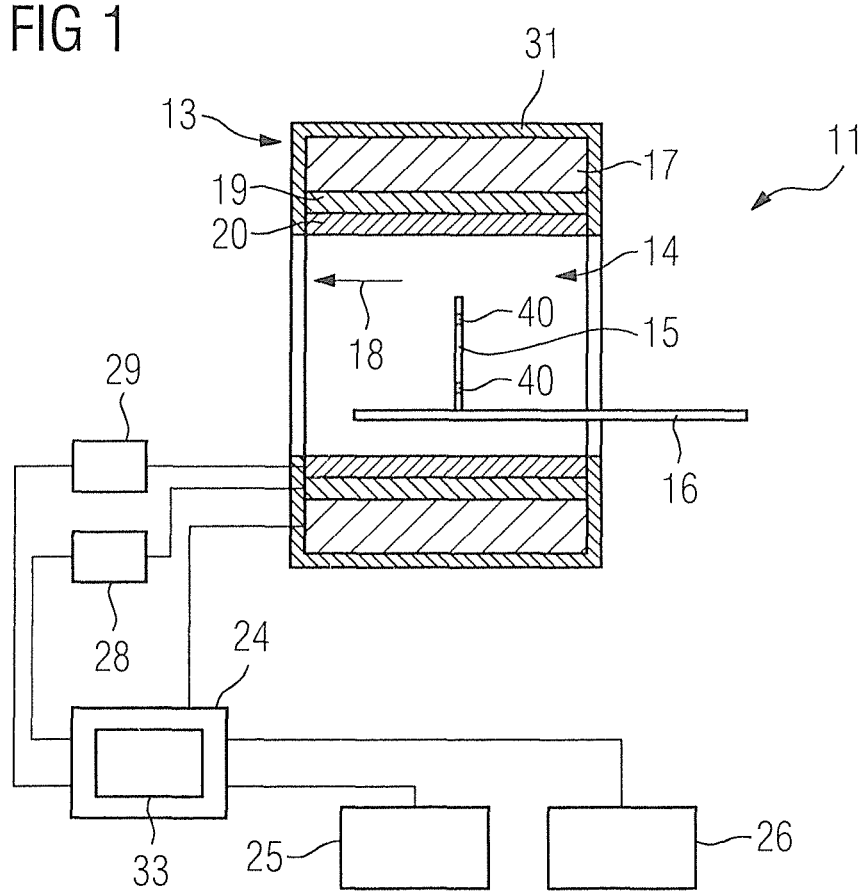
FIG. 1 schematically illustrates a magnetic resonance scanner having a test apparatus according to the invention.

FIG. 1 shows a magnetic resonance apparatus 11 having an inventive test apparatus 15 for use in an inventive method in a schematic representation. In the form illustrated, the test apparatus 15 has two test vessels 40. The number of test vessels 40 is not limited to two, however. The test apparatus 15 may also have further test vessels. The magnetic resonance apparatus 11 has a scanner 13 having a basic field magnet 17 that generates a strong and constant basic magnetic field 18. The basic magnetic field 18 points in a direction that is parallel to an axis. The magnetic resonance scanner 13 has a cylinder-shaped patient receiving zone 14 for accommodating an examination subject. The patient receiving zone 14 is cylindrically enclosed in a circumferential direction by the scanner 13. The test apparatus 15 according to the invention can be introduced into the patient receiving zone 14 by a patient support 16. For this purpose, the patient support 16 has a patient table that is movable inside the magnetic resonance scanner 13. The scanner 13 is shielded externally by a housing enclosure 31.

The scanner 13 additionally has a gradient coil arrangement 19 that is operable to spatially encode MR signals during an imaging session. The gradient coil arrangement 19 is driven by a gradient controller 28. The scanner 13 furthermore has a radio-frequency (RF) antenna 20, which in the case shown is a body coil permanently integrated in the magnetic resonance scanner 13, and a radio-frequency antenna controller 29. The radio-frequency antenna 20 is operated by the radio-frequency antenna controller 29 and radiates radio-frequency (RF) pulses into an examination space that is substantially formed by the patient receiving zone 14. The RF pulses cause the magnetization of nuclear spins within the examination subject to deviate from the alignment or polarization produced by the basic magnetic field 18. As those excited nuclear spins return to the steady state, they emit RF signals called magnetic resonance signals, which are detected by the same that radiated the RF pulses, or by a different antenna. The detected magnetic resonance signals are transformed, in a known manner, into image data.

The magnetic resonance apparatus 11 has a computer 24 that controls the basic field magnet 17, the gradient controller 28 and the radio-frequency antenna controller 29. The computer 24 is responsible for the centralized control of the magnetic resonance apparatus 11, such as for performing MR control sequences. Control information such as imaging parameters, as well as reconstructed magnetic resonance images, may be displayed for a user on a display unit 25, for example on at least one monitor, of the magnetic resonance apparatus 11. The magnetic resonance apparatus 11 additionally has an input interface 26 via which information and/or imaging parameters may be entered by a user during a measurement procedure. The computer 24 may include the gradient controller 28 and/or the radio-frequency antenna controller 29 and/or the display unit 25 and/or the input interface 26. The computer 24 further has a determination processor 33. The magnetic resonance apparatus 11 is therefore configured together with the determination processor 33 and the test apparatus 15 for performing the method according to the invention.

The illustrated magnetic resonance apparatus 11 may of course have further components that are ordinarily present in magnetic resonance apparatuses. The general principles of operation of a magnetic resonance apparatus are known to those skilled in the art, so a more detailed description is not necessary herein.

FIG. 2 shows a flowchart of a first embodiment of the method according to the invention. The method is designed to determine a deviation in homogeneity of a magnetic field of the magnetic resonance scanner 13 in a direction defined by an axis, using at least two test vessels 40 that are arranged on a test plane perpendicular to the direction, by a retaining fixture 21. The method may be performed as follows. In method step 101, the test plane is positioned at a first position 91 of the axis, with the first test vessel thus being at a first location of the first test vessel and the second test vessel being at a first location of the second test vessel. The first position may be specified, for example, by an operator of the magnetic resonance apparatus 11, for example via the input interface 26 of the magnetic resonance apparatus 11. The positioning may be carried out manually by the operator. It is also conceivable for the patient table to be controlled by the determination processor 33, possibly in accordance with a specification by the operator, such that the test apparatus 15 with the test vessels 40 is positioned at the first position 91. The determination processor 33 may also initiate and/or control all of the following positioning steps.

In the following method step 201, measurement data 301 induced by the test vessels 40 at their first locations are recorded. For that purpose, it is typically necessary to operate the magnetic resonance scanner 13 such that MR signals are generated in the test vessels 40, and recorded. This is typically carried out by the computer 24. The recorded measurement data 301 are forwarded to the determination processor 33. The measurement data 301 may designate, for example, the magnitude of the strength of the basic magnetic field 18, or of a gradient field at the locations of the test vessels 40. Alternatively, the measurement data 301 may indicate deviations of the magnetic fields relative to a reference value.

In method step 102, the test plane is positioned at a second position 92 of the axis, which is different from the first position 91 in one coordinate of the first axis, so the first test vessel is then at a second location of the first test vessel and the second test vessel being arranged at a second location of the second test vessel. The positioning is carried out is preferably analogously to method step 101. In the following method step 202, second measurement data 302 induced by the test vessels 40 at their second locations are recorded. Based on at least the first measurement data 301 and the second measurement data 302, the deviation in the homogeneity of the magnetic field is determined in method step 400. This method step is performed by the determination processor 33.

It is also conceivable for measured values of an electromagnetic field, in particular the radio-frequency field used for the excitation in the magnetic resonance imaging session, to be recorded instead of a magnetic field of the magnetic resonance scanner in the direction defined by the axis. The deviation in the homogeneity of the electromagnetic field may be determined based on these measured values.

FIG. 3 shows a flowchart of a second embodiment of the method according to the invention. The second embodiment of the method according to the invention starts with method steps 101, 201, 102 and 202, analogously to the first embodiment illustrated in FIG. 2. Then follows method step 103, the positioning of the test plane at a further position 93 of the axis, which is different from the first position 91 and the second position 92 in one coordinate of the axis. This causes the first test vessel to be at a further location of the first test vessel and the second test vessel to be at a further location of the second test vessel. Further measurement data 303 induced by the test vessels at these further locations are recorded in method step 203. Method steps 103 and 203 may be repeated. In the process, further measurement data may be acquired at further positions. The deviation in the homogeneity of the magnetic field is determined in method step 400 based on at least the first measurement data 301, the second measurement data 302 and the further measurement data 303. This method step is performed by the determination processor 33.

Based on the deviation in the homogeneity of the magnetic field, a number of shim elements and their spatial distribution, i.e. the positions thereof in the scanner 13, are determined in method step 500, in order to increase the homogeneity of the magnetic field. In method step 600, the shim elements determined in method step 500 are arranged at the corresponding positions, typically by a technically competent person, such as an engineer installing the magnetic resonance apparatus 11. The homogeneity of the magnetic field is improved as a result.

Figure 4:
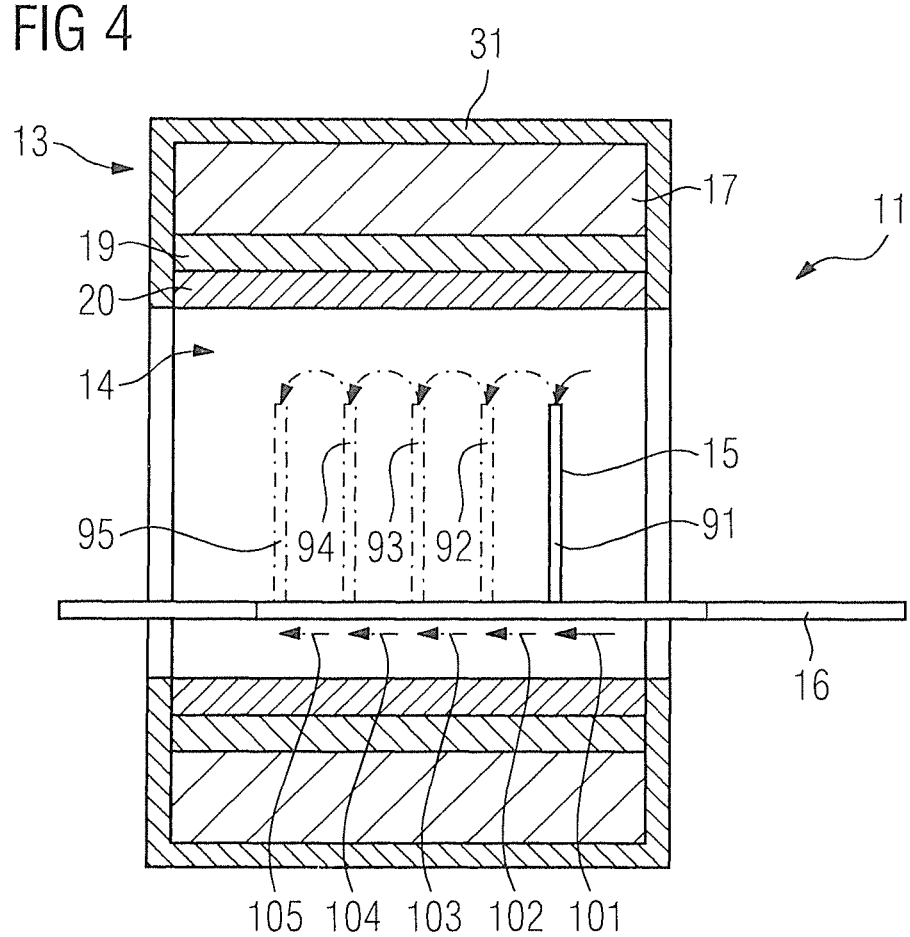
FIG. 4 schematically illustrates a magnetic resonance scanner having a test apparatus according to the invention representation, when the method according to the invention is performed.

FIG. 4 shows a magnetic resonance apparatus 11 having a test apparatus 15 according to the invention in a schematic representation, when the method according to the invention is performed. The test apparatus 15 is arranged on the patient table 16 and may be positioned by the patient table 16 at different positions 91, 92, 93, 94, 95, which differ in one coordinate of the axis-defined direction. The test vessels 40 included in the test apparatus 15 are arranged on a test plane perpendicular to that direction. The positioning steps 101, 102, 103, 104, 105 to place the test apparatus 15 at the first, the second, the further third, the further fourth and the further fifth position 91, 92, 93, 94, 95 may be performed as part of a continuous movement. This means that, for example, the test plane assumes the first position 91 at a first point in time and the second position 92 at a second point in time with no interruption to the continuous movement.

FIG. 5 is a schematic representation of a test apparatus 15 according to the invention. The test vessels 40 included in the test apparatus 15 are mounted on a retaining fixture 21. The test vessels 40 are preferably embodied in a sphere shape. The measurement data 301, 302, 303 induced by the test vessels 40 is recorded by the reception coil unit 12. A commercially available, flexible local reception coil unit 12 may be used in this embodiment. The reception coil unit 12 is preferably arranged such that the reception coil unit 12 substantially encloses the test apparatus 15. To that end the reception coil unit 12 may be arranged on the retaining fixture 21 for the test vessels 40. The test apparatus 15 may also include the reception coil unit 12. In a further embodiment variant (not shown), the reception coil unit 12 is designed such that it has individual reception coils. In this case the number of reception coils preferably corresponds to the number of test vessels 40 and a reception coil is arranged on each test vessel 40. The reception coils may enclose the respective test vessels 40, for example.

The test apparatus illustrated in FIG. 5 has thirteen test vessels 40, which are disposed in a circular arrangement in each case on three concentric circles 51, 52, 53. The number of test vessels 40 is only an example and is not fixed at thirteen. Rather, the test apparatus 15 may have more or fewer test vessels 40. If five positionings of the test plane are carried out according to the inventive method, the intervals between the positions may be chosen such that at each position the test vessels 40 of precisely one circle lie on a spherical surface. Thus, a measured value of the test vessel 40 lying at the center 51 of the test apparatus 15 may be recorded at position 91 shown in FIG. 4, measured values of the test vessels 40 lying on the middle circle 52 may be recorded at position 92 shown in FIG. 4, measured values of the test vessels 40 lying on the outer circle 53 may be recorded at position 93 shown in FIG. 4, measured values of the test vessels 40 lying on the middle circle 52 may be recorded at position 94 shown in FIG. 4, and a measured value of the test vessel 40 lying at the center 51 of the test apparatus 15 may be recorded at position 95 shown in FIG. 4.

In an arrangement of the test vessels 40 of this type, a variable, i.e. changing as a function of the position, subset of the locations of the test vessels at the five positions 91, 92, 93, 94, 95 of the test plane is arranged on a spherical surface. The test apparatus 15 may have at least two different materials. The retaining fixture 21 may have been fabricated from plastic, for example, whereas the test vessels 40 contain liquids. The materials are preferably joined to one another such that they may be separated from one another at predetermined separation points.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for determining a deviation in homogeneity of a basic magnetic field of a magnetic resonance (MR) apparatus, said method comprising:

placing at least two test vessels in an MR data acquisition scanner in a test plane that is perpendicular to a direction defined by an axis in said MR data acquisition scanner;

positioning said test plane at a first position of said axis wherein a first test vessel, of said at least two test vessels, is situated at a first location of the first test vessel and wherein a second test vessel of said at least two test vessels, is situated at a first location of the second test vessel;

operating the MR data acquisition scanner, including generating a basic magnetic field having a homogeneity, to record first measurement data induced by said first and second test vessels at their respective first locations;

repositioning said test plane at a second position of said axis that is different from said first position along one coordinate of said axis, wherein said first test vessel is situated at a second location of the first test vessel and said second test vessel is situated at a second location of said second test vessel;

operating said MR data acquisition scanner to record second measurement data induced by said first and second test vessels at their respective second locations; and providing said first and second measurement data to a processor and, in said processor, determining a deviation of said homogeneity of said basic magnetic field based on at least said first and second measurement data.

2. A method as claimed in claim 1, comprising:

positioning said test plane at at least one further position of said axis, which is different from said first position and said second position in said one coordinate of said axis, wherein said first test vessel is situated at at least one further location of the first test vessel and said second test vessel is situated at at least one further location of the second test vessel;

operating the MR data acquisition scanner to record further measurement data induced by said test vessels at their respective further locations; and in said processor, determining said deviation in the homogeneity of the basic magnetic field based on said first measurement data, said second measurement data and said further measurement data.

3. A method as claimed in claim 1 wherein said MR data acquisition scanner comprises a plurality of shim elements that are selectively positionable within said MR data acquisition scanner to change said homogeneity of said basic magnetic field, and wherein said method comprises:

in said processor, determining at least one of a number of said shim elements and spatial distribution of said shim elements in said MR data acquisition scanner, based on said deviation in said homogeneity of said basic magnetic field, that increases said homogeneity of said basic magnetic field; and emitting an output signal from said processor that electronically designates said at least one of said number of shim elements and said spatial distribution of said shim elements.

4. A method as claimed in claim 1 comprising:

melting said test vessels on a retaining fixture;

situating said retaining fixture on a patient table that is movable within said MR data acquisition scanner; and positioning and repositioning said test plane by moving said patient table within said MR data acquisition scanner.

5. A method as claimed in claim 4 comprising operating said patient table to execute a continuous movement through said MR data acquisition scanner, and thereby causing said test plane to be at said first position at a first point in time and to be at said second position at a second point in time with no interruption of said continuous movement.

6. A method as claimed in claim 1 comprising using test vessels having a spherical shape.

7. A method as claimed in claim 1 comprising recording said first and second measurement data using a reception coil unit of said MR data acquisition scanner.

8. A method as claimed in claim 7 comprising mounting said test vessels on a retaining fixture, and integrating said reception coil unit in said retaining fixture.

9. A method as claimed in claim 1 comprising using at least five test vessels, and arranging said five test vessels in at least one circle in said test plane.

10. A method as claimed in claim 9 comprising arranging said at least five test vessels in at least two concentric circles in said test plane.

11. A method as claimed in claim 1 comprising arranging said test vessels in said test plane and selecting at least said first position in said second position of said test plane, to cause a variable subset of respective locations of said test vessel at said at least first and second positions to be on a spherical surface.

12. A test apparatus for determining a deviation in homogeneity of a basic magnetic field of a magnetic resonance (MR) apparatus, said test apparatus comprising:

a retaining fixture comprising at least two test vessels that is configured to place said at least two test vessels in an MR data acquisition scanner in a test plane that is perpendicular to a direction defined by an axis in said MR data acquisition scanner;

said retaining fixture being configured to position said test plane at a first position of said axis wherein a first test vessel, of said at least two test vessels, is situated at a first location of the first test vessel and wherein a second test vessel of said at least two test vessels, is situated at a first location of the second test vessel; and said retaining fixture being configured to reposition said test plane at a second position of said axis that is different from said first position along one coordinate of said axis, wherein said first test vessel is situated at a second location of the first test vessel and said second test vessel is situated at a second location of said second test vessel.

13. A test apparatus as claimed in claim 12 wherein said test apparatus comprises at least two different materials that are joined to each other in a separable manner, allowing said materials to be separated from each other at a predetermined separation point.

* * * * *